(12) United States Patent
Waller et al.

(10) Patent No.: US 7,640,714 B2
(45) Date of Patent: Jan. 5, 2010

(54) MEDICAL DEVICE PACKAGING ASSEMBLY AND METHOD FOR MEDICAL DEVICE ORIENTATION

(75) Inventors: David F. Waller, Winston-Salem, NC (US); Vihar C. Surti, Winston-Salem, NC (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 256 days.

(21) Appl. No.: 11/527,821

(22) Filed: Sep. 27, 2006

(65) Prior Publication Data

US 2009/0288368 A1    Nov. 26, 2009

Related U.S. Application Data

(60) Provisional application No. 60/722,548, filed on Sep. 30, 2005.

(51) Int. Cl.
*B65B 63/04* (2006.01)
*B65B 55/02* (2006.01)

(52) U.S. Cl. ............................. 53/430; 53/425; 53/469; 206/364

(58) Field of Classification Search ................... 53/430, 53/467, 469, 116, 236, 425; 206/364, 468, 206/564

See application file for complete search history.

(56) References Cited

U.S. PATENT DOCUMENTS

| | | | |
|---|---|---|---|
| 5,344,011 A * | 9/1994 | DiBernardo et al. | 206/364 |
| 5,372,254 A | 12/1994 | Gross | |
| 5,568,865 A * | 10/1996 | Mase et al. | 206/438 |
| 5,846,259 A * | 12/1998 | Berthiaume | 606/192 |
| 5,848,691 A * | 12/1998 | Morris et al. | 206/364 |
| 6,053,313 A * | 4/2000 | Farrell et al. | 206/364 |
| 6,375,006 B1 * | 4/2002 | Samuels | 206/364 |
| 6,719,135 B2 * | 4/2004 | Armijo | 206/364 |
| 6,902,057 B2 | 6/2005 | Duffy | |
| 7,000,770 B2 * | 2/2006 | Clarke et al. | 206/571 |
| 7,104,399 B2 * | 9/2006 | Duffy et al. | 206/364 |
| 7,334,678 B2 * | 2/2008 | Kesler et al. | 206/364 |
| 2004/0055919 A1 | 3/2004 | Rowe et al. | |
| 2004/0055926 A1 | 3/2004 | Duffy et al. | |
| 2004/0144667 A1 | 7/2004 | Duffy | |
| 2005/0061698 A1 | 3/2005 | Delaney et al. | |

FOREIGN PATENT DOCUMENTS

WO    WO 98/18515 A1    5/1998

* cited by examiner

*Primary Examiner*—Paul R Durand
(74) *Attorney, Agent, or Firm*—Brinks Hofer Gilson & Lione (57) ABSTRACT

Methods of packaging a medical device to orient at least a portion of the medical device and a medical device packaging assembly are provided. A method includes providing an elongate holder having a lumen extending through at least a portion of the holder and providing the medical device including an elongate shaft where the shaft includes a first cross-sectional area having a rotational orientation and a second cross-sectional area having a second rotational orientation. The method further includes aligning the first and second areas so that the first and second rotational orientations are aligned along a longitudinal region of the shaft and inserting at least a portion of the medical device into the lumen of the holder Radial rotation of the first area with respect to the second area is substantially prevented.

14 Claims, 8 Drawing Sheets

MEDICAL DEVICE PACKAGING ASSEMBLY AND METHOD FOR MEDICAL DEVICE ORIENTATION

RELATED APPLICATIONS

This application claims the benefit of U.S. Provisional Application No. 60/722,548, filed Sep. 30, 2005, which is incorporated herein in its entirety.

FIELD OF THE INVENTION

The present invention relates to packaging for a medical device, and more particularly to packaging and methods for packaging for elongate medical devices including catheters and the like, wherein the orientation for at least a portion of the device is maintained.

BACKGROUND

A variety of elongated and generally hollow medical devices exist that can be introduced into a patient for many different purposes. For example, elongate medical devices may be used to supply therapeutic fluids, to perform diagnostic or surgical procedures, for implantation of therapeutic devices, and for the introduction of instruments. Exemplary devices include catheters, cannulae, papillotomes, sphincterotomes and the like. The medical devices have a variety of shapes and sizes, and generally include an elongated shaft ranging in length from several inches to several feet long. The diameter of the shaft of the device is usually much smaller than its length. The medical devices typically include one or more lumens extending through most or all of the length of the shaft of the device. One of the lumens may be used for insertion of a wire guide or similar device along the length of the lumen. The medical devices also generally include a distal end which may be shaped or configured as required to carry out the specific procedure for which the device is designed. For example, the distal end may include a complex curvature, adapted to the specific geometry of a target area in the body to facilitate reaching the target location or to facilitate carrying out the procedure.

These medical devices are typically packaged for sterilization and shipping. Generally, the packaging provides protection for the medical device and ensures sterility of the device upon delivery to the end user. For example, the elongate shaft of the medical device may be provided in a coiled configuration to make the device more compact for placement in a sterilization pouch and to save room for shipping and storage. These types of packages for sterilization and storage, including packages for coiled configurations, for elongate medical devices are known in the art. However, a previously unrecognized problem arises in the known packaging systems wherein the elongate medical devices become twisted or kinked before or during sterilization or storage, thus rendering these medical devices unusable for the intended medical procedure. In some packaging systems, automated feeding of the elongate medical device into a package prior to sterilization and storage may also cause twisting or kinking of the elongate portion of the device.

During the sterilization process and during storage after manufacture, the overall shape of these medical devices will often change. For example, during the ethylene gas sterilization of the medical devices, portions of these devices, such as the elongate shaft will often increase in length, twist or both, while the distal tip may lose its preformed shape. For medical devices formed from a urethane material, sterilization after manufacture and packaging may include the application of heat. However, the elevated temperature used during sterilization causes the urethane material to relax and twist. The changes in shape and length of the medical devices caused by the sterilization processes, such as ethylene gas and heat, are non-uniform and will vary between each individual medical device. These individual variations due to sterilization cannot be compensated for during the manufacturing process. Some of these changes may make it difficult for the end user to properly use the device. For example, when the lumen the medical device is twisted, insertion or removal of the wire guide may be impaired.

What is needed is an improved packaging system and method for elongate medical devices that maintains the orientation of one or more lumens or portions of the elongate shaft by orienting the elongate shaft in the packaging system prior to sterilization and storage to minimizing twisting or kinking of the shaft during sterilization, shipping and storage.

BRIEF SUMMARY

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

In one aspect of the present invention a method of packaging a medical device to orient at least a portion of the medical device is provided. The method includes providing an elongate holder having a lumen extending through at least a portion of the holder and providing a medical device including an elongate shaft, the shaft comprising a first cross-sectional area having a first rotational orientation and a second cross-sectional area having a second rotational orientation. The method includes aligning the first and second cross-sectional areas of the shaft so that the first and second rotational orientations are aligned along a longitudinal region of the shaft and inserting at least a portion of the medical device into the lumen of the holder so that the portion of the medical device inserted into the holder maintains the alignment of the first and second rotational orientations and radial rotation of the first cross-sectional area with respect to the second cross-sectional area is substantially prevented.

In another aspect of the present invention, a method of packaging a medical device to orient at least a portion of the medical device is provided. The method includes providing a holder having a lumen extending therethrough and providing the medical device including an elongate shaft where the shaft includes a splittable wall region along a longitudinal region. The method further includes radially orienting a first area of the splittable wall region with a second area along the longitudinal region; and inserting at least a portion of the shaft into the holder so that the first and second area of the splittable wall region remain substantially radially oriented along the longitudinal region without radial rotation of the splittable wall region in the holder.

In yet another aspect of the present invention, a medical device packaging assembly is provided. The assembly includes an elongate holder having a lumen where the lumen extends through at least a portion of the holder. The assembly also includes a medical device having an elongate shaft. The shaft includes a first area having first rotational orientation and a second area having a second rotational orientation, at least a portion of the shaft being received in the lumen of the holder so that the rotational orientation of the first area and the rotational orientation of the second area are aligned along a longitudinal region of the shaft without radial rotation of the first area with respect to the second area when the shaft is received in the lumen of the holder.

BRIEF DESCRIPTION OF THE DRAWINGS

Embodiments of the present invention will now be described by way of example with reference to the accompanying drawings, in which.

DETAILED DESCRIPTION OF THE INVENTION

Figure 1:
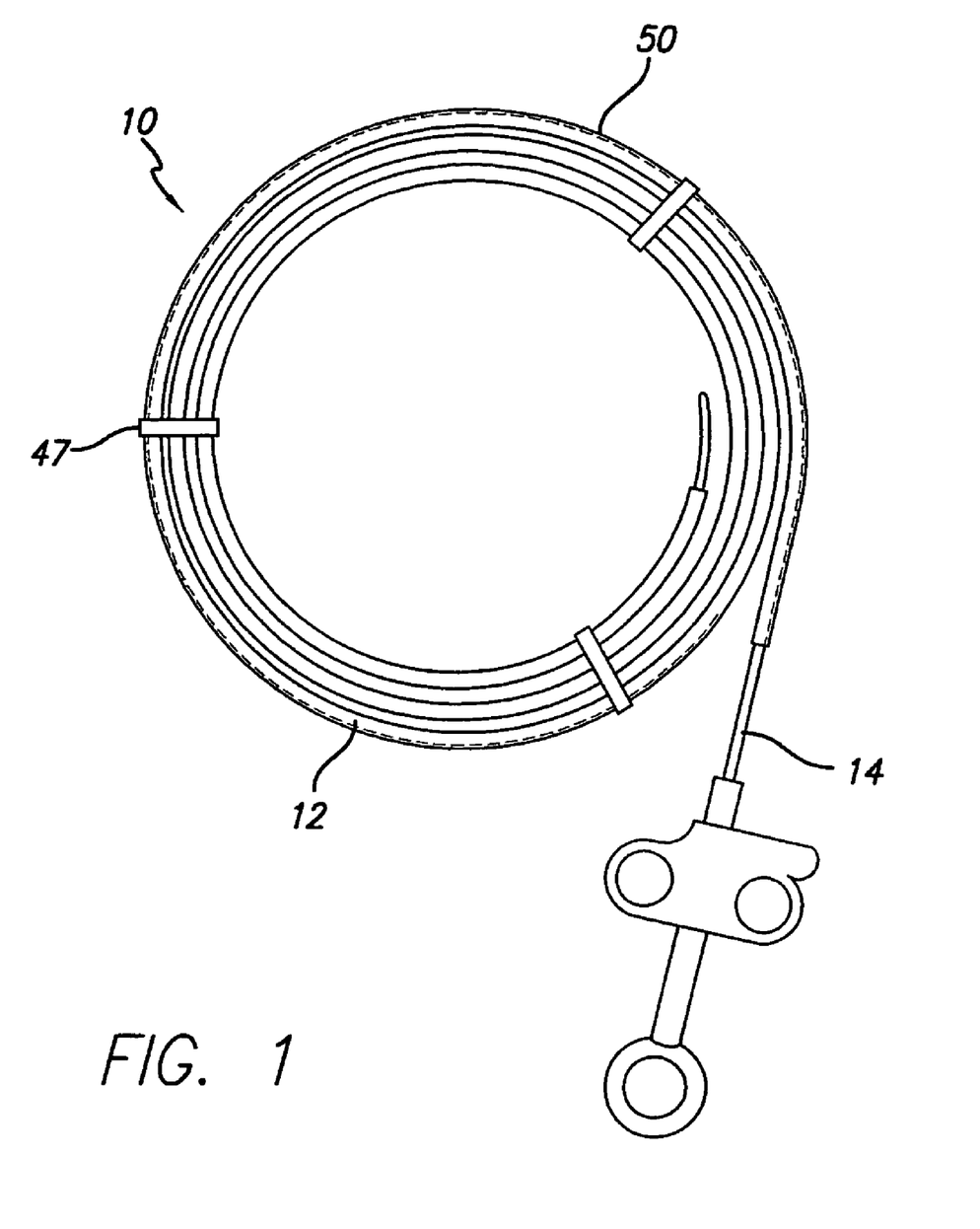
FIG. 1 is a side view of a medical device packaging assembly according to an embodiment of the present invention.

A medical device packaging assembly 10 of the present invention is illustrated in FIG. 1. As shown in FIG. 1, the assembly 10 includes a holder 12 and an elongate medical device 14. Exemplary elongate medical devices that may be used with the holder 12 include, but are not limited to, catheters, cannulas, sphincterotomes, papillotomes or the like.

Figure 2A:
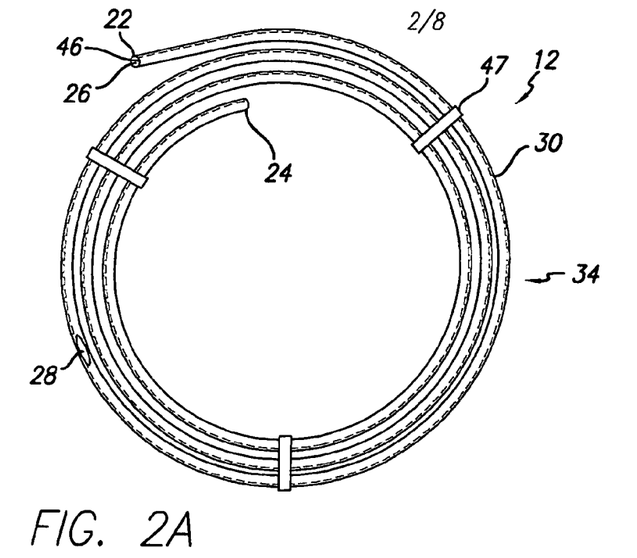
FIG. 2A is a side view of a planar, coiled holder of the packaging assembly shown in FIG. 1.
Figure 2B:
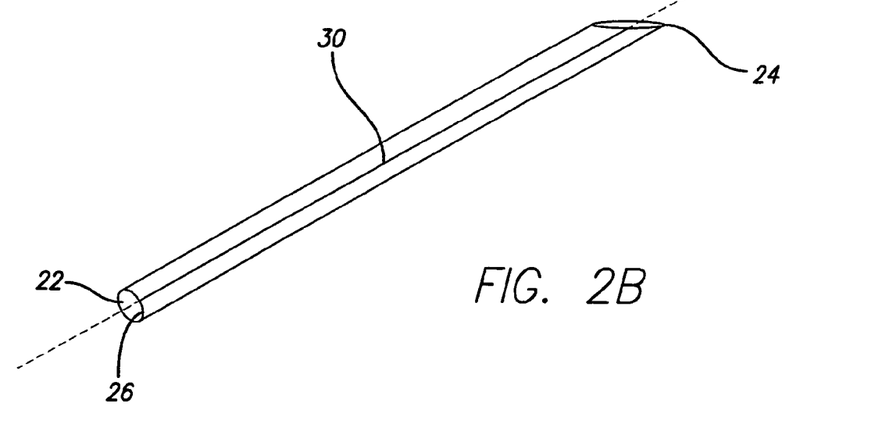
FIG. 2B is a perspective view of a linear holder of the packaging assembly of the present invention.

The holder 12 is illustrated in FIGS. 2A and 2B. The holder 12 may be provided in different configurations as will be understood by one skilled in the art, including a planar coil (2A), a helical coil, a hoop, a straight configuration (2B), and the like. The holder 12 includes a first end 22 and a second end 24 as shown in FIGS. 2A and 2B. The holder 12 further includes a lumen 26 extending through the holder 12 between the first end 22 and the second end 24. In some embodiments, the lumen 26 may extend partially through the holder 12, for example, where the holder 12 includes a closed first end 22 or second end 26 or where the holder 12 includes an opening 28 between the first end 22 and the second end 24. The holder 26 includes a longitudinal axis 29 and may include a longitudinal region 30 extending along the holder 12, as shown in FIG. 2B, between the first end 22 and the second end 24.

Figure 2C:
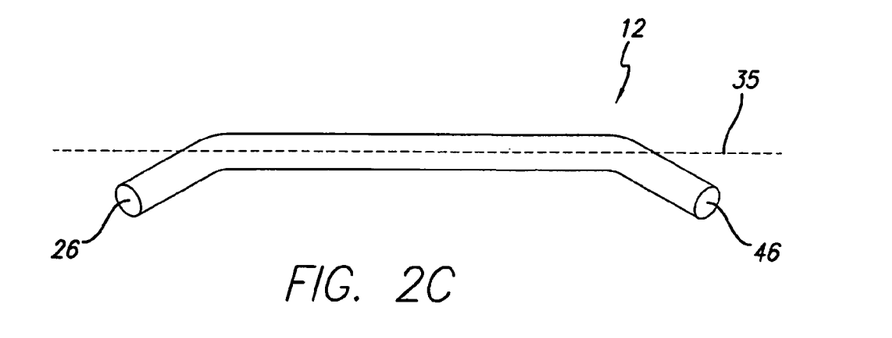
FIG. 2C is a side view of a portion of the holder shown in FIG. 2A.

In some embodiments of the present invention, the longitudinal region may be on the exterior facing portion 34 of the coiled holder 12 as shown in FIG. 2A. When the holder 12 is provided in a coiled configuration as shown in FIG. 2A, the longitudinal region 30 is in a single plane 35 (FIG. 2C). In the example of a helical coil, the region 30 may face outward from the center of the coil. The holder 12 may be held in a non-linear configuration by clips, adhesive, bonding, such as heat or sonic bonding, and the like. Exemplary clips 47 are shown in FIG. 2A where the clips 47 include recesses to releasably hold the holder 12 in a coil. A plurality of clips 47 may be used and spaced apart to hold the holder 12 in a desired configuration as will be understood by one skilled in the art.

Figure 3A:
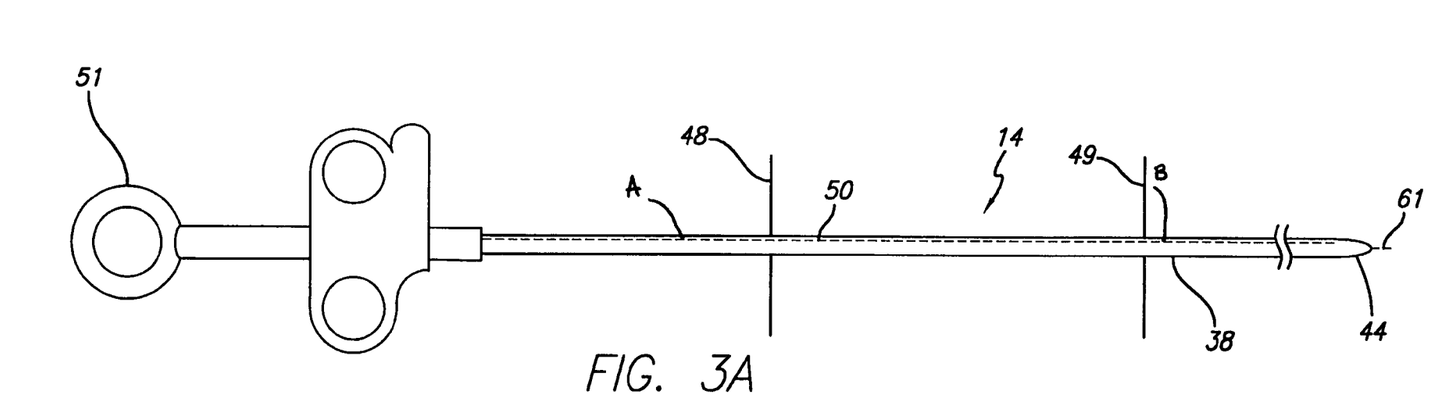
FIG. 3A is a side view of a medical device having an elongate shaft for assembly with the holder shown in FIG. 2.

The lumen 26 of the holder 12 may be sized and shaped to receive an elongate shaft 38 of a medical device 14, such as the device shown in FIG. 3A. The dimensions of the holder 12 will vary depending on the size and configuration of the elongate shaft 38 of the medical device 14. For example, the diameter of the elongate shaft 38 may range from 1 French to 20 French. A distal end 44 of the shaft 38 may include additional elements such as connectors, stylets, mandrels, needles, tubing, wires and the like. Non-limiting, exemplary medical devices that include features such as an elongate shaft include Fusion OMNI E.R.C.P. Catheters and Sphincterotomes (Wilson-Cook, Inc.), GLO-TIP II® E.R.C.P. Catheters (Wilson-Cook, Inc.), METRO® Wire Guide (Wilson-Cook, Inc.) and the like.

The lumen 26 of the holder 12 will be sized and shaped to slidably accommodate at least a portion of the shaft 38 and any additional elements connected to distal end 44 of the medical device 14, which are typically collapsible so as to pass through the lumen 26. In some embodiments, the holder 12 may be provided in a cylindrical configuration having a cylindrical cross-sectional lumen 26 in a cylindrical cross-sectional tubing forming the holder 12 as shown in FIGS. 2A and 2B. However, additional configurations for the cross-sectional shape of the lumen and the holder are possible including, but not limited to, oval, square, rectangular, triangular and combinations thereof. An inner diameter 46 of the lumen 26 will be sized and shaped for insertion of the shaft 38 of the medical device 14 and will minimize radial twisting movement of the shaft 38 within the holder 14. For example, the lumen 26 having a cylindrical cross-sectional shape may have an inner diameter 46 from about 0.030 inches to about 0.300 inches. The outer diameter of the holder 12 may range from about 0.100 inches to about 0.500 inches in some embodiments. In some embodiments, the ratio of the outer diameter of the shaft 38 to the holder 12 may be about 1:1.2 to about 1:4.

The length of the holder 12 will vary depending on the length of the medical device 14. In some embodiments, the holder 12 may extend the entire length of the shaft 38 of the medical device 14 while in other embodiments, the holder 12 may extend over a partial length of the shaft 38. The distal portion 44 of the medical device 14 may extend through the lumen 26 and out through the second end 24 of the holder 12. Additional elements may be added to the distal end 44 of the shaft 38 after the shaft 38 has been inserted into the holder 12 and the distal end 44 extends out through the second end of the holder 12. For example, where the medical device 14 is a sphincterotome, a shaping wire (not shown) may be inserted into the distal end 44 of the shaft 38. In some embodiments, the second end 24 of the holder 12 may be sealed and the distal end 44 of the elongate medical device 14 may be enclosed within the holder 12. Preferably, the holder 12 extends over at least 70% of the elongate shaft 38 of the medical device 14.

The holder 12 may be formed from any suitable material for slidably receiving the shaft 38 of the medical device 14. The holder 12 may be formed from plastic materials, such as polyethylene, polycarbonate, polyvinyl chloride, polyurethane, from metal or metal alloy materials and other suitable materials. An example of a suitable holder may be made from high density polyethylene (HDPE) and purchased from Coeur, Inc., Washington, N.C.

Figure 3B:
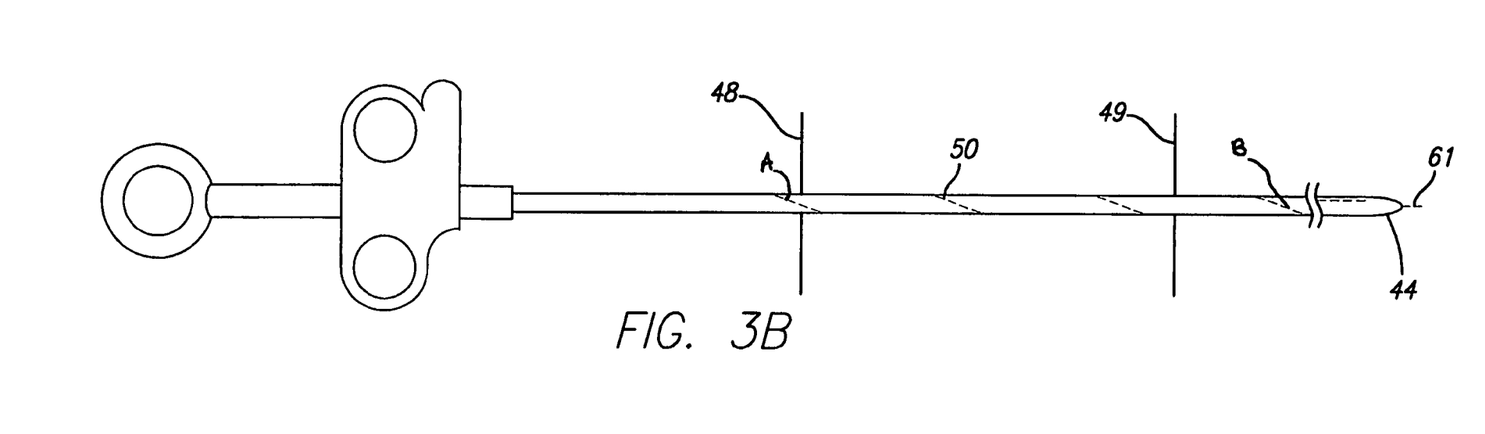
FIG. 3B is a side view of a medical device having an radially twisted elongate shaft.
Figure 4A:
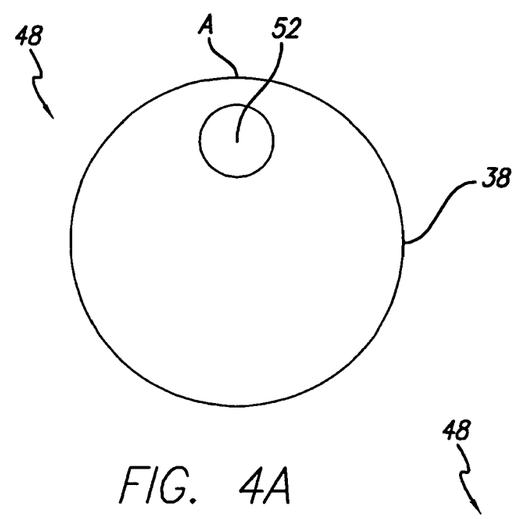
FIG. 4A is a cross-sectional view of the elongate shaft of the medical device.
Figure 4B:
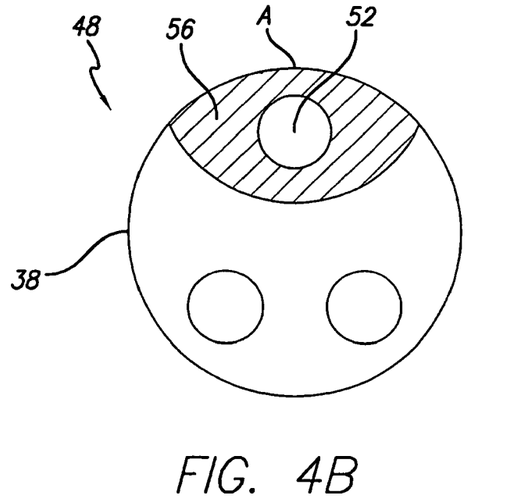
FIG. 4B is a cross-sectional view of an alternative embodiment of the elongate shaft of the medical device.
Figure 4C:
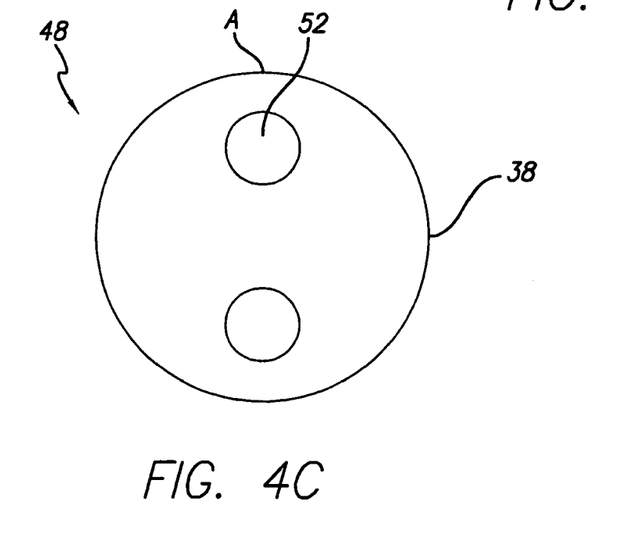
FIG. 4C is a cross-sectional view of an alternative embodiment of the elongate shaft of the medical device.
Figure 6:
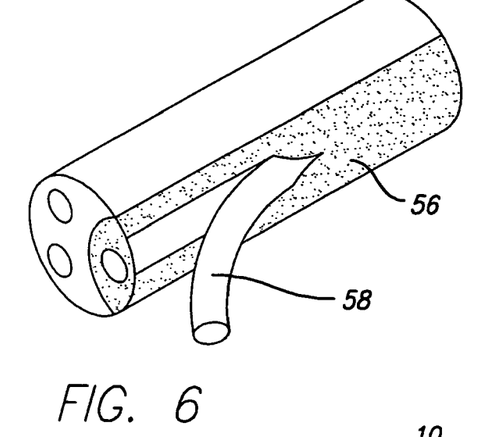
FIG. 6 is a perspective view of the elongate shaft shown in FIG. 4B.

As shown in FIGS. 3A and 3B, the elongate shaft 38 of the medical device 14 includes a longitudinal region 50. The shaft 38 also includes a first cross-sectional area 48 having a first rotational orientation and a second cross-sectional area 49 having a second rotational orientation positioned along the shaft 38 between a proximal end 51 and the distal end 44. The first and second cross-sectional areas 48, 49 may be located anywhere along the elongate shaft 38 and are used to illustrate twisting or rotation of the elongate shaft 38 at a first area A with respect to a second area B, spaced apart form the first area A, elongate shaft 38. For example, the first cross-sectional area 48 may be located closer to the proximal end 51 and the second cross-sectional area 49 may be located closer to the distal end 44 as shown in FIG. 3A. The first cross-sectional area, 48, the second cross-sectional area 49, or both may include a lumen 52 extending therethrough. A view of the first cross-sectional area 48 illustrating the lumen 52 in the shaft 38 is shown in FIGS. 4A-4C. In some embodiments, a single lumen, a dual lumen or a plurality of lumens may be included in the shaft 38. The lumens may have the same or different sizes and shaped, depending on the purpose of the lumen, including passage of medical devices and fluids to an internal location in the patient. The lumen 52 may be adapted to receive a wire guide or the like for operation of the medical device 14. In some embodiments, the shaft 38 may include a splittable wall region 56 having the lumen 52 therein as shown in FIGS. 4B and 6. The splittable wall region 56 may have a sufficiently thin region 56 forming the wall or the region 56 may be formed a lower durometer material where the region 56 permits a wire guide 58 to readily tear or split through the region 56 as the medical device 14 is being removed from the patient as shown in FIG. 6. In some embodiments, the shaft 38 may comprise a coextruded shaft material wherein the material surrounding the lumen 52 is selected or adapted to facilitate splittability for removal of a medical device, such as a wire guide. For example, the coextruded shaft may be formed from a plurality of materials where one of the material has a lower durometer to facilitate splittability. Exemplary coextruded shafts are manufactured by Zeus Industrial Products, Inc. (Orangeburg, S.C.).

Figure 5A:
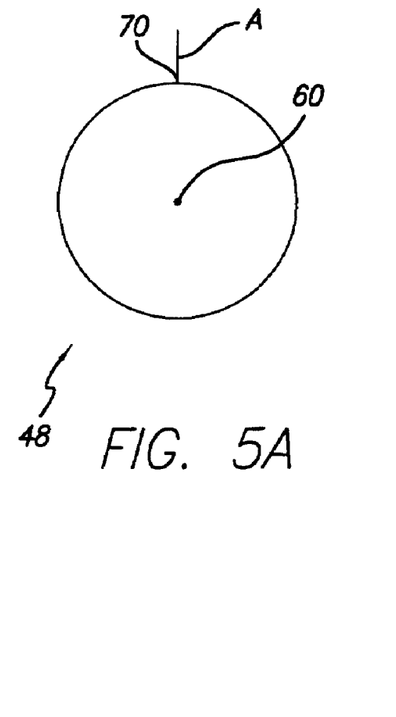
FIG. 5A is a cross-sectional view of a first cross-sectional area shown in FIG. 3A.
Figure 5B:
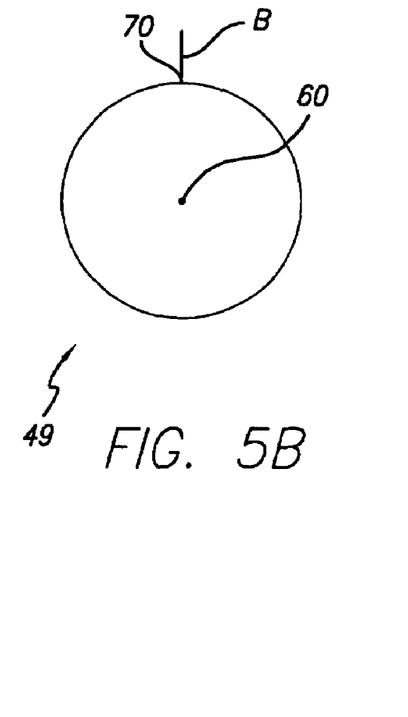
FIG. 5B is a cross-sectional view of a second cross-sectional area shown in FIG. 3A.
Figure 5C:
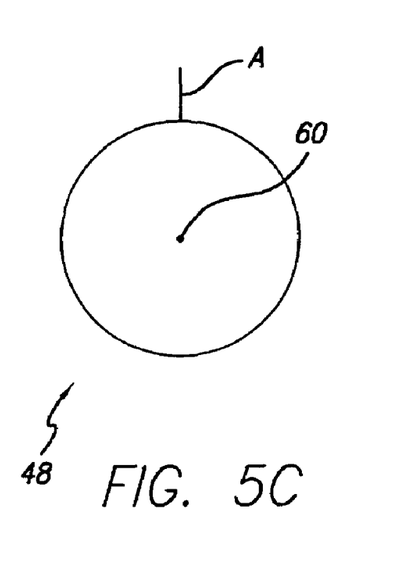
FIG. 5C is a cross-sectional view of the first cross-sectional area shown in FIG. 3B.
Figure 5D:
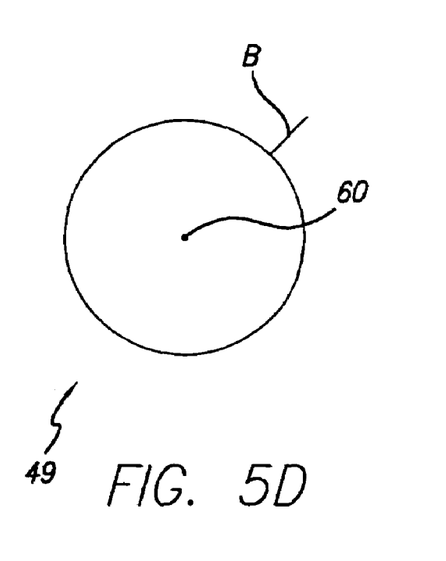
FIG. 5D is a cross-sectional view of the second cross-sectional area shown in FIG. 3B.

In some embodiments, it is desirable to provide the elongate shaft 38 of the medical device 14 wherein the rotational orientation of area A of the first cross-sectional area 48 may be aligned with the rotational orientation of area B of the second cross-sectional area 49 and the aligned areas A and B of the first and second cross-sectional areas 48, 49 extend along the longitudinal region 50 of the shaft 38. As shown in FIG. 3A, the shaft 38 extends in a linear configuration and the area A and the area B of the cross-sectional areas 48, 49, respectively are aligned. The alignment of the areas A and B depicted in FIG. 3A is shown in cross sectional views in FIGS. 5A and 5B and may be maintained when the shaft 38 is longitudinally coiled into a planar coil configuration. FIG. 3B illustrates a twisted shaft 38 where the shaft 38 rotates radially about the axis 60 extending through the shaft 38. As shown in cross-section in FIGS. 5C and 5D, the rotational orientation of area B of the second cross-sectional area 49 is radially rotated with respect to the rotational orientation of area A of the first cross-sectional area 48. When the second cross-sectional area 49 rotates radially with respect to the first cross-sectional area 48, the first and second rotational orientations are not aligned along the longitudinal region 50 and the shaft 38 becomes twisted or kinked making it more difficult or impossible for the user to operate the medical device 14. For example, when the shaft 38 includes a splittable wall region 56 having a wire guide 58, the wire guide 58 may not readily tear through the wall region 56 if the shaft 38 is radially twisted around the axis 60 as illustrated in FIGS. 5C and 5D where the areas A and B are radially rotated with respect to each other. Twisting or kinking of the shaft 38 may occur during packaging, sterilizing, storage and the like, of the medical device 14.

Figure 7:
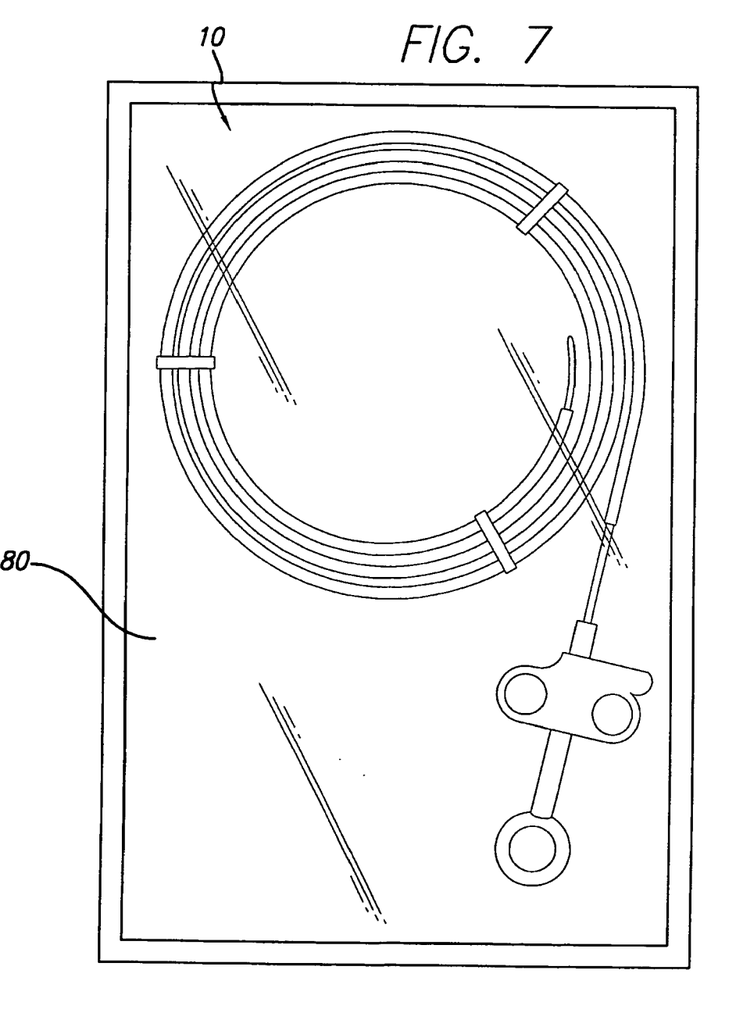
FIG. 7 is a side view of the packaging assembly shown in FIG. 1 including a pouch.

As illustrated in FIG. 1, the packaging assembly 10 secures the medical device 14 in the holder 12 so that the area A of the first cross-sectional area 48 and the area B of the second cross sectional area of the shaft 38 of the medical device 14 are oriented along the longitudinal axis 60. The packaging assembly 10 may include an exterior package for packaging, sterilization and storage of the assembly 10. Any type of packaging suitable for sterilization and storage may be used with the present invention as will be understood by one skilled in the art. As shown in FIG. 7, a pouch 80 may be provided for enclosing the assembly 10. The pouch 80 may be formed from materials suitable for allowing and maintaining sterilization of the assembly 10 within the pouch 80. Any suitable material known to one skilled in the art may be used, including, but not limited to gas permeable, medical grade sheets, such as transparent polymeric sheets. The pouch 80 may be formed having a backing comprising a paper or TYVEK® sheet that is secured to the polymeric sheet such as by heat-sealing or bonding. The pouch 80 may be suitable for sterilization by heat, ethylene oxide, gamma irradiation, and the like.

In operation, the holder 12 may be provided for assembly with the medical device in any configuration. In some embodiments, and as shown in FIG. 2A, the holder 12 may be provided in a planar, coiled configuration with a plurality of clips 47 releasably holding the holder 12 in the coiled configuration. As shown in FIG. 2A, both ends 22 and 24 may be open, forming the lumen 26.

Figure 8A:
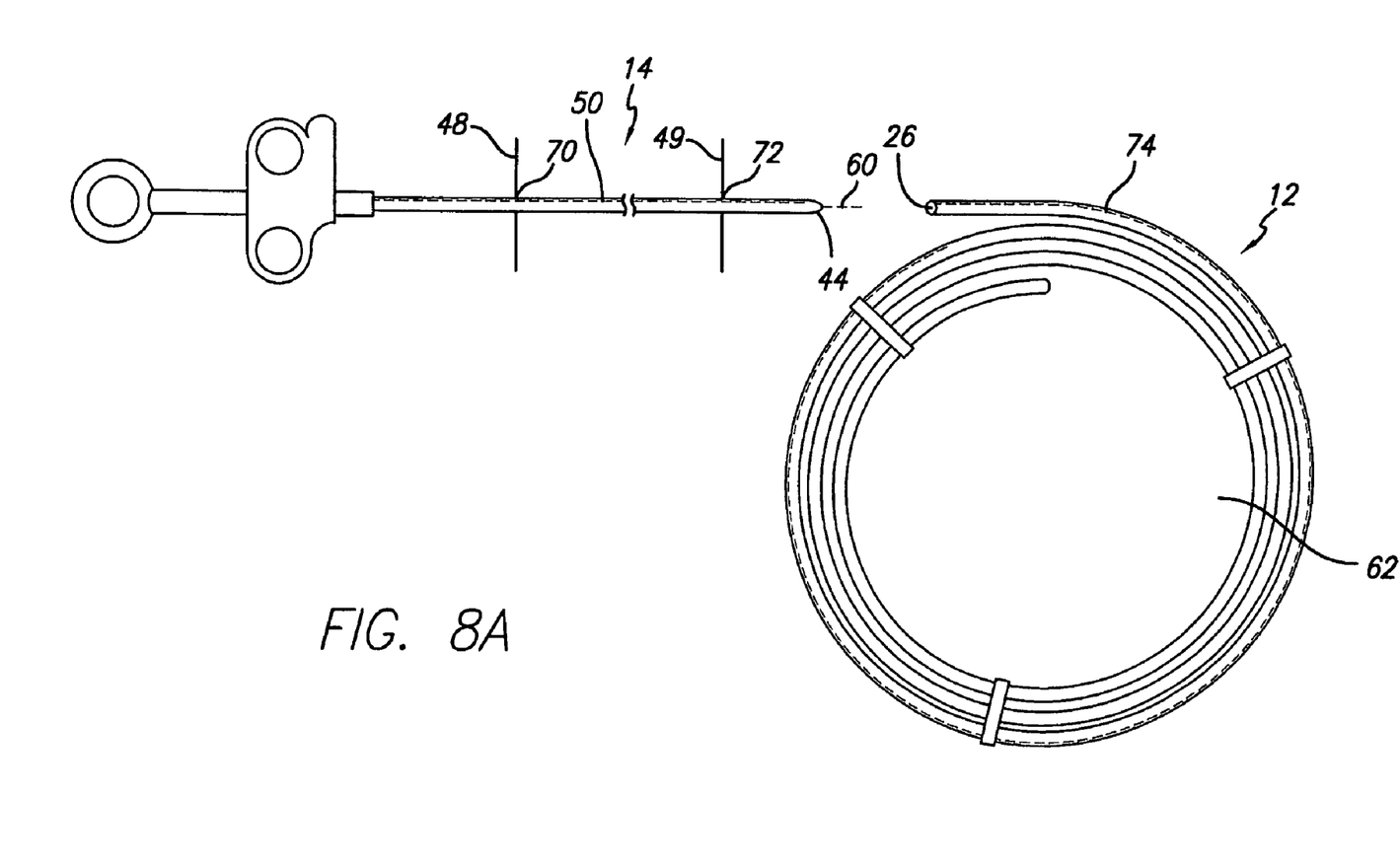
FIG. 8A is a side view of the medical device oriented for insertion into the holder.
Figure 8B:
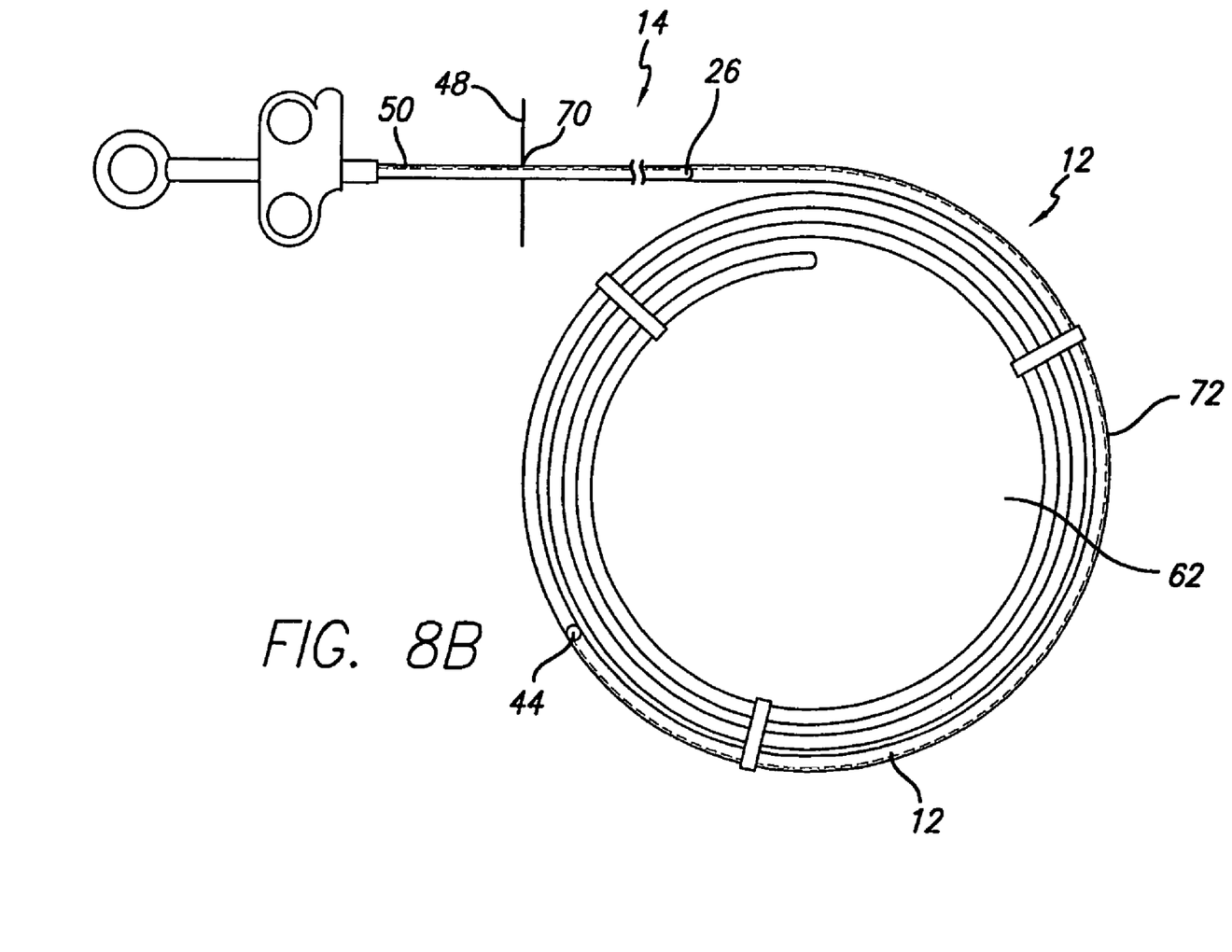
FIG. 8B is a side view of the medical device partially inserted into the holder.

The medical device 14 is provided for insertion of at least a portion of the shaft 38 of the medical device 14 into the lumen 26 of the holder 12. For insertion into the holder 12, the area A of the first cross-sectional area 48 and the area B of the second cross-sectional area 49 of the shaft 38 are aligned with each other and parallel to the axis 60 of the shaft 38, as shown in FIG. 8A, so that the area A of the first cross-sectional area 48 and the area B of the second cross-sectional area 49 of the shaft 38 will align in the holder 12 with the shaft 38 forming a linear coil, substantially preventing axial rotation of the shaft 38 about the axis 60. In some embodiments, the shaft 38 may be inserted into the holder 12 so that the area A of the first cross-sectional area 48 and the area B of the second cross-sectional area 49 of the shaft 38 are aligned with the longitudinal region 30 of the holder 12. The shaft 38, the holder 12, or both may be provided with markings along the longitudinal region 30, at the area A, or at the area B, or combinations thereof, to guide alignment as the shaft 38 is slidably inserted into the lumen 26 of the holder 12. The area A of the first cross-sectional area 48 or the area B of the second cross-sectional area 49 may be used as a guide align the shaft 38 as the shaft 38 is slidably received in the holder 12. For example, when the shaft 38 includes a splittable wall region 56 having the areas A or B or both, the region 56 may have a different color than the remainder of the shaft 38. The colored wall region 56 may be used to align itself as the distal portion 44 of the shaft begins to pass the end 22 of the holder 12 into the lumen 26 where the shaft 38 continues to be inserted shown in 8B. For example, if the wall region 56 is oriented to the exterior 34 of the holder 12 with the areas A and B facing outward from a center of the coil 62, as the shaft 38 is inserted into the holder 12, the areas A and B may be monitored and oriented to the exterior 34 as the shaft 38 is further slidably received in the holder 12.

The holder 12 may also include markings along the longitudinal region 30 that may be colored for visually aligning the shaft 38 in the holder 12. The area A of the first cross-sectional area 48 or the area B of the second cross-sectional area 49, or both, of the medical device 15 may include markings that are visible through the holder 12 when the holder 12 is formed from a translucent material and the holder need not include markings for alignment. For example, the area A may include a first marking 70 and the area B may include a second marking 72 that may be aligned prior to assembling the elongate shaft 38 into the holder 12, as shown in FIG. 8A. The holder 12 may also include a third marking 74 that may be used to align the first marking 70 the second marking 72 or both in the holder 12. The third marking 74 on the holder may be a single marking or a longitudinal marking, for example along the longitudinal region 30. The markings 70, 72 may be single marking or alternatively, the markings 70, 72 may extend along the shaft 38 along the longitudinal region 50. The markings 70, 72 need not be used for identifying the position of the elongate shaft 38 within the body, for example similar to radiopaque markers known in the art. Any markings known to one of skill in the art may be used to guide alignment of the area A of the first cross-sectional area 48 and the area B of the second cross-sectional area 49 of the shaft 38 with the longitudinal region 30 of the holder 12.

In some embodiments, the shaft 38 of the medical device 14 is manually inserted into the lumen 26 of the holder 12. An operator inserting the shaft 38 orients the area A of the first cross-sectional area 48 and the area B of the second cross-sectional area 49 to be parallel to the axis 60 and removes any radial twisting in the shaft 38. The operator monitors the longitudinal orientation of the shaft 38 as the shaft 38 is inserted into the holder 12 to be sure that the orientation is maintained as the shaft 38 is slidably received in the lumen 26. The operator may make adjustments to the orientation of the shaft 38 as the shaft 38 is inserted. Alternatively, the shaft 38 of the medical device 14 may be automatically inserted into the holder 12 after being oriented to longitudinally align the longitudinal region 50.

After insertion of the portion of the shaft 38 into the holder 12 has been completed, the assembly 10 may be packaged into the pouch 80 for sterilization and storage. Any type of sterilization procedure known to one of skill in the art for sterilizing medical devices may be used. The sterilized assembly 10 may be stored in the pouch 80 until use in a medical procedure.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. The scope of the invention is defined by the appended claims, and all devices that come within the meaning of the claims, either literally or by equivalence, are intended to be embraced therein.

Any other undisclosed or incidental details of the construction or composition of the various elements of the disclosed embodiment of the present invention or methods of their use are not believed to be critical to the achievement of the advantages of the present invention, so long as the elements possess the attributes need to perform as disclosed. The selection of these and other details of construction are believed to be well within the ability of one of even rudimentary skills in this area, in view of the present disclosure. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition.

The invention claimed is:

1. A method of packaging a medical device to orient at least a portion of the medical device, the method comprising:
   providing a holder in a coiled configuration, the holder having a lumen extending therethrough;
   providing the medical device comprising an elongate shaft, the shaft comprising a splittable wall region along a longitudinal region;
   radially orienting a first area of the splittable wall region with a second area along the longitudinal region; and
   inserting at least a portion of the shaft into the holder so that the first and second area of the splittable wall region remain substantially radially oriented along the longitudinal region without radial rotation of the splittable wall region in the holder.

2. The method of claim 1, further comprising providing a pouch for receiving the holder and the medical device.

3. The method of claim 2, further comprising sterilizing the holder and the medical device in the pouch.

4. The method of claim 1, comprising manually inserting the portion of the medical device into the holder.

5. The method of claim 1, wherein at least 70% of the device is inserted into the holder.

6. The method of claim 1, further comprising adjusting the alignment of the first area with respect to the second area as the portion of the medical device is being inserted into the lumen to maintain the alignment of the splittable wall region and substantially prevent radial rotation of the splittable wall region in the holder.

7. A method of packaging a medical device to orient at least a portion of the medical device, the method comprising:
   providing an elongate holder in a coiled configuration, the holder comprising a lumen extending through at least a Portion of the holder;
   providing the medical device comprising an elongate shaft, the shaft comprising a first cross-sectional area having a first rotational orientation and a second cross-sectional area having a second rotational orientation;
   aligning the first and second cross-sectional areas of the shaft so that the first and second rotational orientations are aligned along a longitudinal region of the shaft; and
   inserting at least a portion of the medical device into the lumen of the holder so that the portion of the medical device inserted into the holder maintains the alignment of the first and second rotational orientations and radial rotation of the first cross-sectional area with respect to the second cross-sectional area is substantially prevented.

8. The method of claim 7, wherein the coiled configuration is planar.

9. The method of claim 7, further comprising providing a pouch for receiving the holder and the medical device.

10. The method of claim 9, further comprising sterilizing the holder and the medical device in the pouch.

11. The method of claim 7, further comprising providing at least one marking on the medical device for aligning the device in the holder.

12. The method of claim 7, comprising manually inserting the portion of the medical device into the holder to align the first area with the second cross-sectional area in the holder.

13. The method of claim 7, wherein at least 70% of the shaft is inserted in to the holder with the first area and the second cross-sectional area aligned.

14. The method of claim 7, further comprising monitoring the alignment of the first cross-sectional area with respect to the second cross sectional area as the portion of the medical device is being inserted into the lumen of the holder.

* * * * *

UNITED STATES PATENT AND TRADEMARK OFFICE
CERTIFICATE OF CORRECTION

PATENT NO. : 7,640,714 B2  Page 1 of 1
APPLICATION NO. : 11/527821
DATED : January 5, 2010
INVENTOR(S) : Waller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 356 days.

Signed and Sealed this

Sixteenth Day of November, 2010

David J. Kappos
*Director of the United States Patent and Trademark Office*